(12) United States Patent
Zhang et al.

(10) Patent No.: US 9,434,702 B2
(45) Date of Patent: Sep. 6, 2016

(54) METHOD FOR PREPARING LINEZOLID INTERMEDIATE

(71) Applicants: Zhejiang Hisun Pharmaceutical Co., Ltd., Zhejiang (CN); Shanghai Institute of Pharmaceutical Industry, Shanghai (CN)

(72) Inventors: Fuli Zhang, Shangai (CN); Chunbo Yang, Shangai (CN); Bin Liang, Shangai (CN); Pengcheng Qiu, Shangai (CN); Hairong Luo, Zhejiang (CN); Jiang Li, Zhejiang (CN); Jian Chai, Zhejiang (CN); Qingfeng Cai, Zhejiang (CN)

(73) Assignees: Zhejiang Hisun Pharamceutical Co., Ltd. (CN); Shanghai Institute of Pharmaceutical Industry (CN)

( * ) Notice: Subject to any disclaimer, the term of this patent is extended or adjusted under 35 U.S.C. 154(b) by 21 days.

(21) Appl. No.: 14/378,825

(22) PCT Filed: Feb. 8, 2013

(86) PCT No.: PCT/CN2013/071576
§ 371 (c)(1),
(2) Date: Aug. 14, 2014

(87) PCT Pub. No.: WO2013/120448
PCT Pub. Date: Aug. 22, 2013

(65) Prior Publication Data
US 2015/0011757 A1    Jan. 8, 2015

(30) Foreign Application Priority Data

Feb. 15, 2012 (CN) .......................... 2012 1 0038198.3

(51) Int. Cl.
C07D 413/06     (2006.01)
C07D 263/20     (2006.01)

(52) U.S. Cl.
CPC ........... *C07D 263/20* (2013.01); *C07D 413/06* (2013.01)

(58) Field of Classification Search
None
See application file for complete search history.

(56) References Cited

U.S. PATENT DOCUMENTS

2007/0032472 A1    2/2007    Mohan Rao et al.

FOREIGN PATENT DOCUMENTS

| CN | 1772750 A | 5/2006 |
|---|---|---|
| CN | 102250076 A | 11/2011 |
| CN | 102702125 A | * 10/2012 |
| EP | 1403267 A1 | 3/2004 |
| WO | 9507271 A1 | 3/1995 |
| WO | 2007116284 A1 | 10/2007 |
| WO | 2011098501 A1 | 8/2011 |
| WO | 2011137222 A1 | 11/2011 |

OTHER PUBLICATIONS

An English translation of CN 102702125 A (Zhu et al.), 2012.*
Chinese Journal of Medicinal Chemistry, pp. 287-289, 20 (4), 2010, English translation of Abstract only.
Gregory Walter A et al. Antivacterials. synthesis and structure-activity studies of 3-aryl-2-oxooxazolidines. 2. The "A" group. J.Med.Chem. 1990, No. 33, pp. 2569 to 2578.
International Search Report for Application No. PCT/CN2013/071576 dated May 9, 2013.

* cited by examiner

*Primary Examiner* — Laura L. Stockton
(74) *Attorney, Agent, or Firm* — Lerner, David, Littenberg, Krumholz & Mentlik, LLP

(57) ABSTRACT

Disclosed is a new method for preparing a methyl substitute of a linezolid intermediate, (S)-2-(3-(3-fluoro-4-morpholinophenyl)-2-oxo-5-oxazoline) (I), wherein the intermediate (I) is obtained by the cyclization of 3-fluoro-4-morpholinophenyl isocyanate (II) and epoxy compound (III). This process has a short process route, low cost, easy operation, and high yield, so is suitable for a large-scale industrial production.

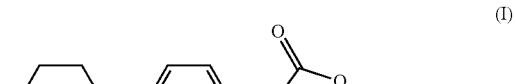

(I)

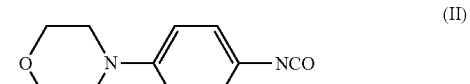

(II)

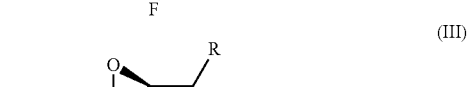

(III)

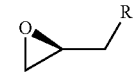

9 Claims, No Drawings

METHOD FOR PREPARING LINEZOLID INTERMEDIATE

CROSS-REFERENCE TO RELATED APPLICATION

The present application is a national phase entry under 35 U.S.C. §371 of International Application No. PCT/CN2013/071576, filed Feb. 8, 2013, published in English, which claims priority from Chinese Patent Application No. 201210038198.3, filed Feb. 15, 2012.

FIELD OF THE INVENTION

The present invention relates to a novel process for preparing a pharmaceutical intermediate. Specifically, it relates to a novel synthetic process of a key intermediate, a methyl substitute of (S)-2-(3-(3-fluoro-4-morpholinophenyl)-2-oxo-5-oxazoline) (I), which is involved in the process of synthesizing an antibiotic, i.e., linezolid.

BACKGROUND OF THE INVENTION

Linezolid, with the chemical name of (S)—N-{[3-(3-fluoro-4-(4-morpholinophenyl)-2-oxo-5-oxazoline)]methyl}-acetamide, has a structure as shown in Formula (IV)

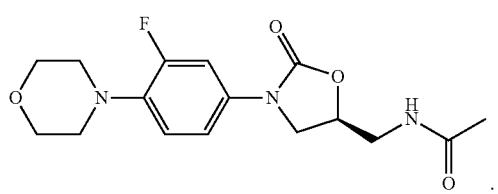

Linezolid is a novel oxazolidinone-type antibiotic, which is developed by Pharmacia & Upjohn Company (P&U). Linezolid takes effect on the ribosome of bacteria, and inhibits the synthesis of bacterial protein. Linezolid is mainly used in the treatment of bacteremia caused by vancomycin-resistant enterococci (VRE), pneumonia and complicated skin infections caused by methicillin-resistant *Staphylococcus aureus* (MRSA), and bacteremia caused by penicillin resistant *Streptococcus pneumonia* (PRSP).

A methyl substitute of (S)-2-(3-(3-fluoro-4-morpholinophenyl)-2-oxo-5-oxazoline) is the key intermediate in the synthesis of linezolid, wherein the structure is as shown in Formula (I). Linezolid can be obtained by treating the intermediate with a deprotective agent followed by acetylation.

At present, several methods for preparing linezolid as follows are reported:

1. WO957271 reports a synthetic route as follows:

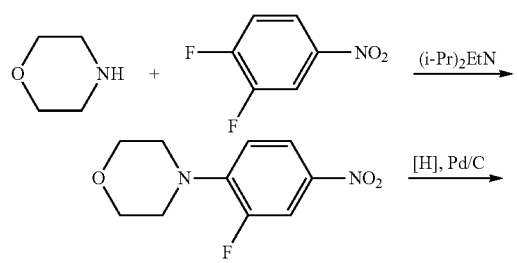

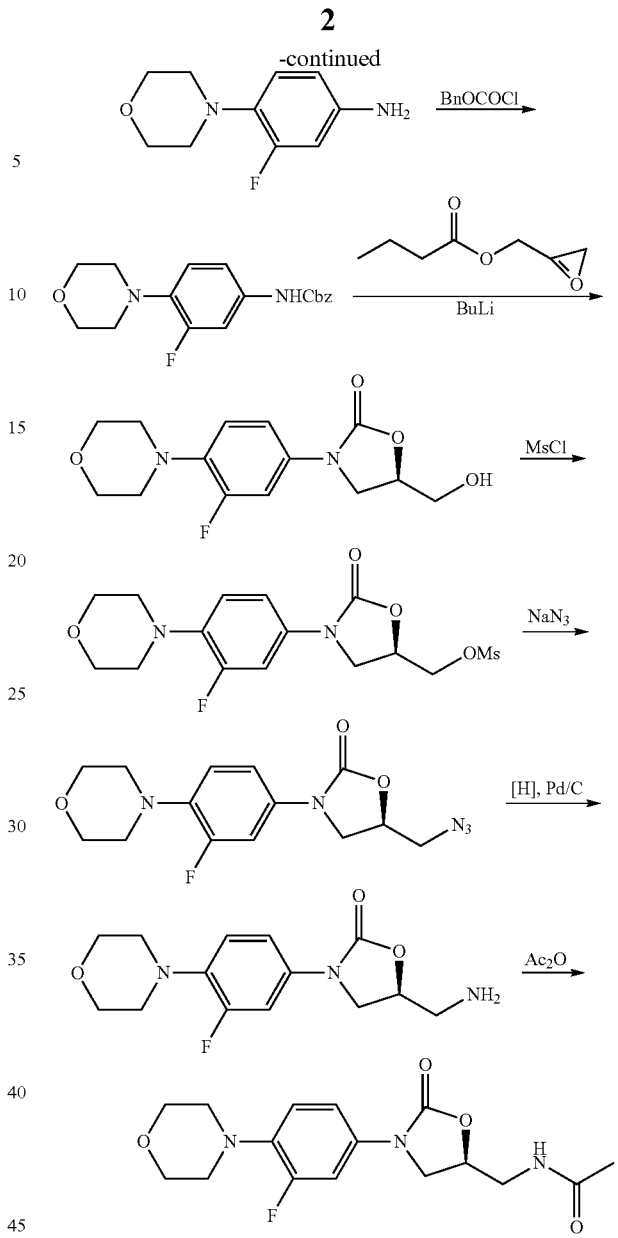

This route is relatively long and requires utilization of dangerous agents such as butyllithium, sodium azide and the like. In addition, the cyclization reaction needs a low temperature as −78° C. The subsequent hydrogenation needs a high pressure, which demands high requirements for the equipment used in the course of synthesis. Accordingly, this route is not suitable for an industrial production.

2. CN1772750 reports a synthetic route as follows:

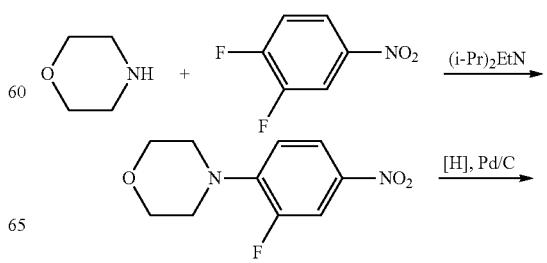

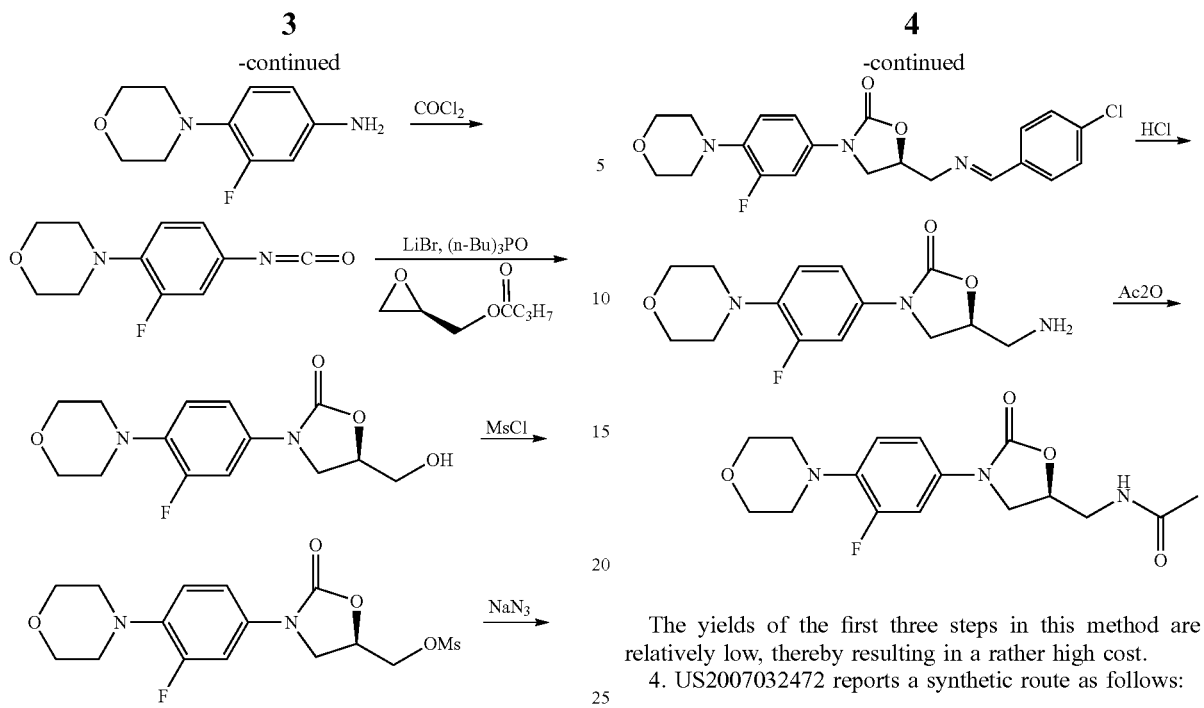

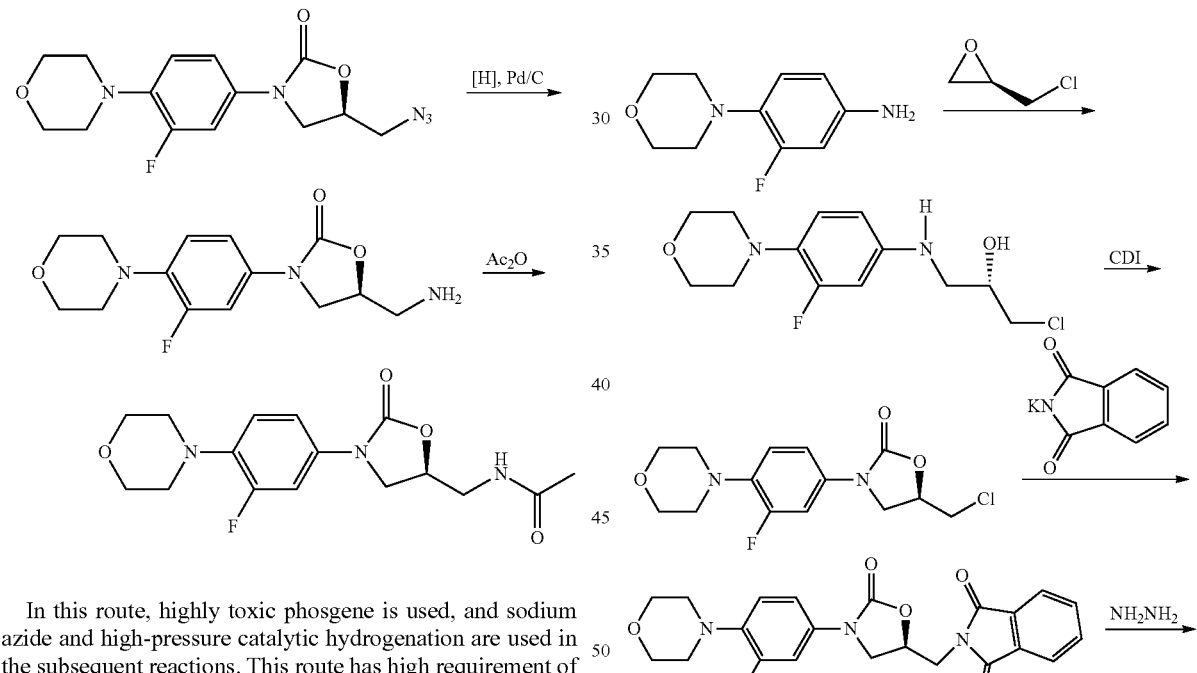

In this route, highly toxic phosgene is used, and sodium azide and high-pressure catalytic hydrogenation are used in the subsequent reactions. This route has high requirement of the equipment and has some potential safety hazards, thus it is not suitable for an industrial production.

3. WO2007116284 reports a synthetic route as follows:

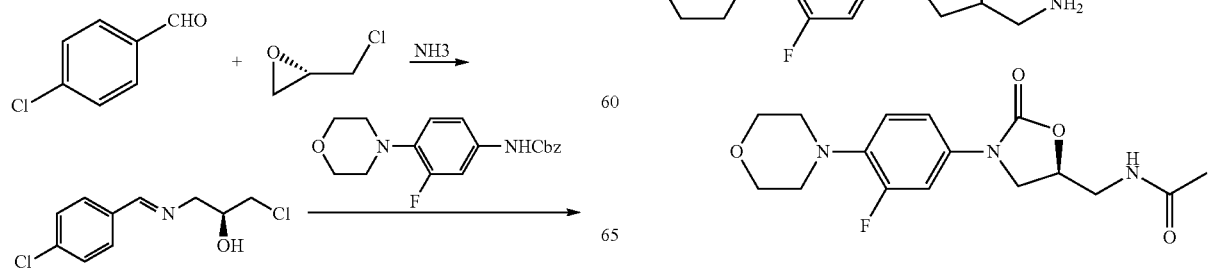

The yields of the first three steps in this method are relatively low, thereby resulting in a rather high cost.

4. US2007032472 reports a synthetic route as follows:

The yield of the first step in this route is relatively low, and an inversion of configuration might easily happen. The ratio of products to isomers is about 85:15, wherein the isomers are difficult to separate and will be brought into the subsequent reactions till the final product (i.e., linezolid), thereby affecting the product quality.

SUMMARY OF THE INVENTION

The technical problem to be solved by the present invention is to overcome the defects in the present processes for preparing linezolid, such as severe conditions, high requirements for the equipment, a potential safety hazard, low yields, difficulty in separating the by-products, high costs, complex processes, and not suitable for an industrial production, etc.

The present invention provides a novel process of preparing the key intermediate (I) which is suitable for an industrial production.

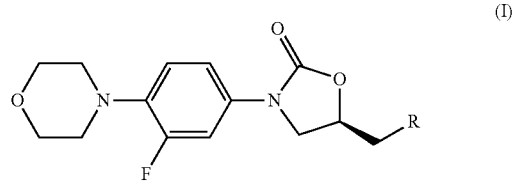

(I)

This process comprises the following steps:

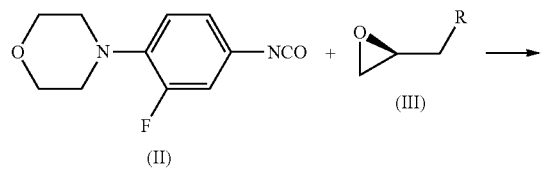

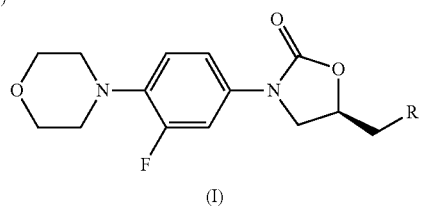

(I)

The compound of Formula (I) is obtained by a cyclization reaction of 3-fluoro-4-morpholinophenyl isocyanate (II) and epoxy compound (III) in the presence of a reaction solvent and a catalyst.

Wherein the compound of Formula (II) can be prepared by the method described in Chinese Journal of Medicinal Chemistry, pages 287-289, 20 (4), 2010.

In the compound of Formula (III), R group is a protected amino group. The term "protected" used herein has a common meaning known in the art. That is, in order to prevent a group from being broken by a reaction, the group is firstly protected, and then deprotected after the reaction completes.

R group is preferably chosen from the following groups:

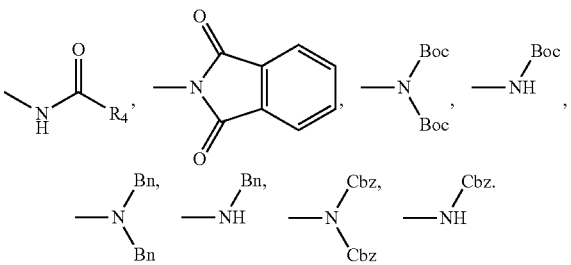

wherein $R_1$ is hydrogen or $C_{1-6}$ alkyl, and Boc represents tert-butoxycarbonyl group, Bn represents benzyl group, Cbz represents benzyloxycarbonyl group, wherein Boc represents tert-butoxycarbonyl group, Bn represents benzyl group, Cbz represents benzyloxycarbonyl group, most preferably, wherein R is phthalimidyl, and the whole structure (I-1) is as follows:

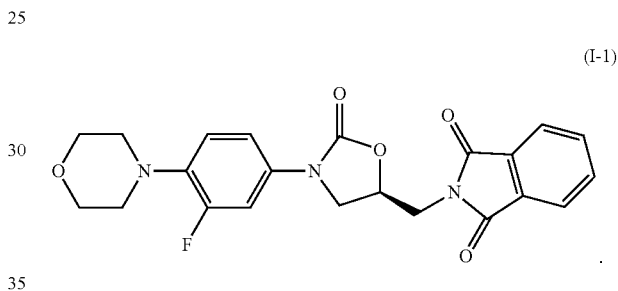

The methyl substitute of (S)-2-(3-(3-fluoro-4-morpholinophenyl)-2-oxo-5-oxazoline)) with the structure as shown by Formula (I) is the key intermediate in the process of synthesizing linezolid. The intermediate can be deprotected according to the method described in US2007032472 and the conventional methods of removing the protective groups known by a person skilled in the art, followed by acetylation to obtain linezolid.

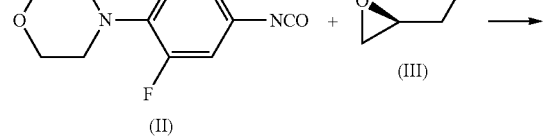

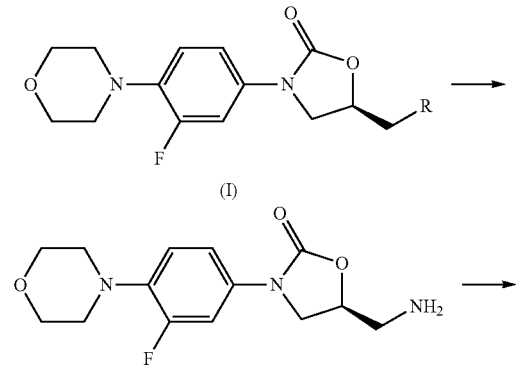

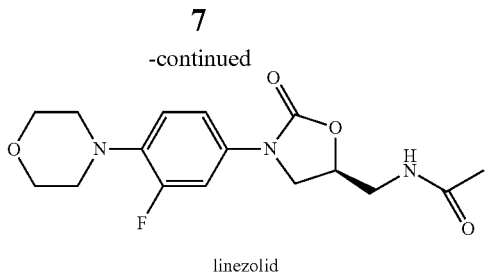

linezolid

For example, when R is phthalimidyl, linezolid can be prepared by subsequent reactions as follows:

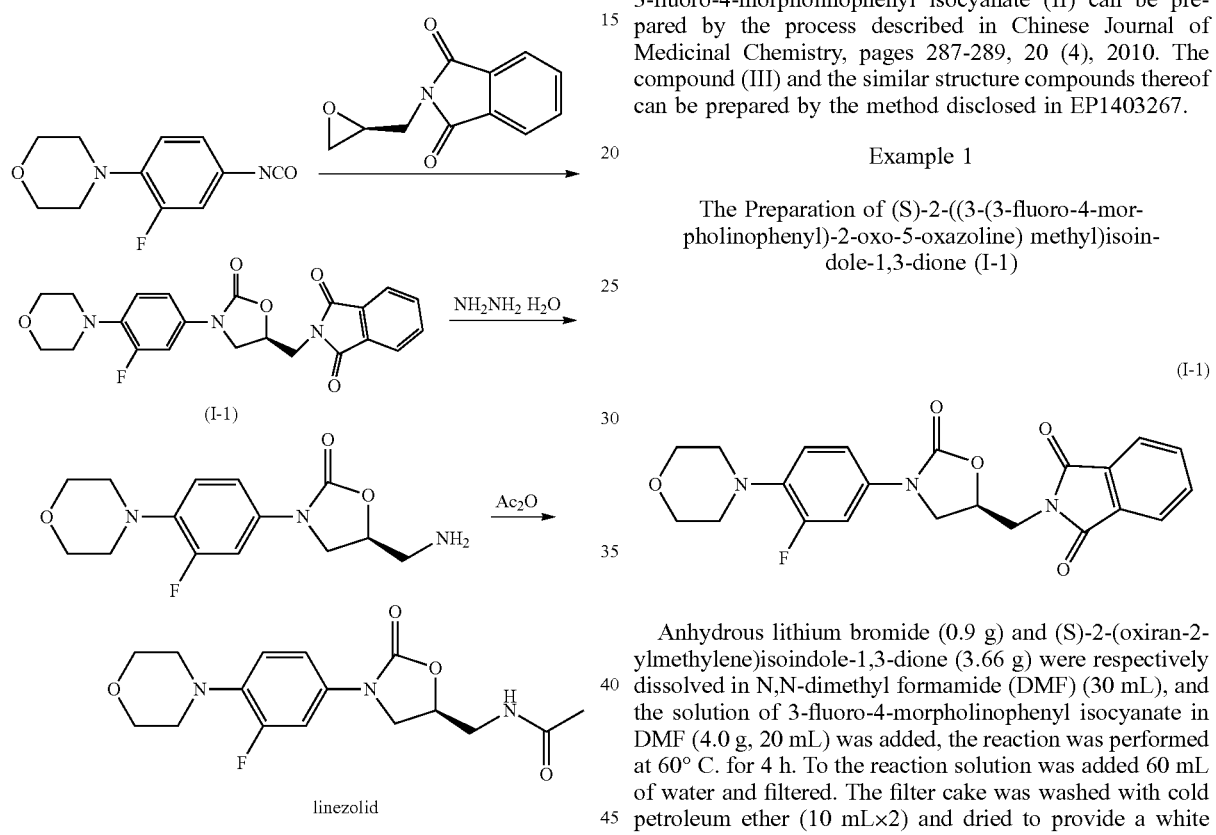

linezolid

In one embodiment, the catalyst used in the cyclization reaction of the present invention is a Lewis acid or a mixture thereof, wherein the Lewis acid includes but not limited to lithium bromide, magnesium bromide, lithium chloride, magnesium chloride, magnesium iodide, lithium iodide, lithium chloride, zinc chloride, tetra-n-butylammonium bromide, tetra-n-butylammonium chloride, or a mixture thereof, preferably lithium bromide, magnesium bromide, magnesium iodide and the like, or any mixture thereof.

In one embodiment, the solvent used in the cyclization reaction of the present invention is an aprotic solvent or a mixture thereof, wherein the aprotic solvent includes but not limited to ethyl acetate, butyl acetate, isoamyl acetate, toluene, xylene, chlorobenzene, tetrahydrofuran, dichloromethane, N,N-dimethylformamide, $C_6$-$C_8$ alkanes, acetone, 1,4-dioxane, acetonitrile or a mixture thereof, preferably butyl acetate, xylene, N,N-dimethylformamide, tetrahydrofuran and the like, or any mixture thereof.

In one embodiment, the temperature of the cyclization reaction in the present invention is 60° C.-150° C., preferably 100-140° C., particularly preferably 115-125° C.

Comparing with the prior art, the present invention has the following advantages: the improved process is simple, the reaction is mild, the total yield is high, the product has good purity, and it does not require the utilization of hazardous agents (such as, butyl lithium, sodium azide) as well as it does not require severe conditions (such as ultra-low temperatures, etc.). Thus, the method of the present invention is suitable for an industrial production.

DETAILED EMBODIMENTS

The present invention is further illustrated by but not limited to the following examples. In which, the compound 3-fluoro-4-morpholinophenyl isocyanate (II) can be prepared by the process described in Chinese Journal of Medicinal Chemistry, pages 287-289, 20 (4), 2010. The compound (III) and the similar structure compounds thereof can be prepared by the method disclosed in EP1403267.

Example 1

The Preparation of (S)-2-((3-(3-fluoro-4-morpholinophenyl)-2-oxo-5-oxazoline) methyl)isoindole-1,3-dione (I-1)

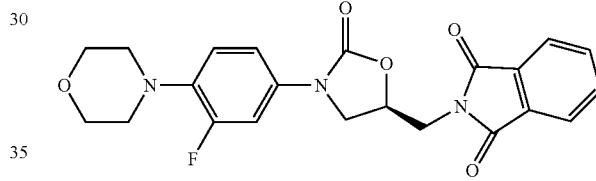

Anhydrous lithium bromide (0.9 g) and (S)-2-(oxiran-2-ylmethylene)isoindole-1,3-dione (3.66 g) were respectively dissolved in N,N-dimethyl formamide (DMF) (30 mL), and the solution of 3-fluoro-4-morpholinophenyl isocyanate in DMF (4.0 g, 20 mL) was added, the reaction was performed at 60° C. for 4 h. To the reaction solution was added 60 mL of water and filtered. The filter cake was washed with cold petroleum ether (10 mL×2) and dried to provide a white solid 6.90 g with a yield of 90.11%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 2

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in DMF (30 mL), and the solution of 3-fluoro-4-morpholinophenyl isocyanate in DMF (4.0 g, 20 mL) was added. The reaction was performed at 100° C. for 4 h. To the reaction solution was added 60 mL of water and filtered. The filter cake was washed with cold petroleum ether (10 mL×2) and dried to provide a white solid 7.10 g with a yield of 92.72%.

ESI-MS (m/z): 426 (M+H), 448 (M+Na);

¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 3

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in DMF (30 mL), and the solution of 3-fluoro-4-morpholinophenyl isocyanate in DMF (4.0 g, 20 mL) was added. The reaction was performed at 115° C. for 4 h. To the reaction solution was added 60 mL of water and filtered. The filter cake was washed with cold petroleum ether (10 mL×2), and dried to provide a white solid 7.29 g with a yield of 95.16%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 4

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in DMF (30 mL), and the solution of 3-fluoro-4-morpholinophenyl isocyanate in DMF (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.32 g with a yield of 95.59%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 5

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxirane-2-methylene)isoindole-1,3-dione (3.66 g) were respectively dissolved in DMF (30 mL), and the solution of 3-fluoro-4-morpholino phenyl isocyanate in DMF (4.0 g, 20 mL) was added. The reaction was performed at 125° C. for 4 h. To the reaction solution was added 60 mL of water and filtered. The filter cake was washed with cold petroleum ether (10 mL×2) and dried to provide a white solid 7.30 g with a yield of 95.30%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 6

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in DMF (30 mL), and the solution of 3-fluoro-4-morpholino phenyl isocyanate in DMF (4.0 g, 20 mL) was added. The reaction was performed at 140° C. for 4 h. To the reaction solution was added 60 mL of water and filtered. The filter cake was washed with cold petroleum ether (10 mL×2) and dried to provide a white solid 7.19 g with a yield of 93.89%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 7

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in DMF (30 mL), and the solution of 3-fluoro-4-morpholino phenyl isocyanate in DMF (4.0 g, 20 mL) was added. The reaction was performed at 150° C. for 4 h. To the reaction solution was added 60 mL of water and filtered. The filter cake was washed with cold petroleum ether (10 mL×2) and dried to provide a white solid 7.05 g with a yield of 92.07%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 8

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in tetrahydrofuran (THF) (30 mL), and the solution of 3-fluoro-4-morpholinophenyl isocyanate in THF (4.0 g, 20 mL) was added. The reaction was performed under reflux for 4 h. The reaction solution was concentrated to dryness, and then was added 60 mL of water and extracted with CH₂Cl₂ (60 mL×2). The organic layer was dried over anhydrous sodium sulfate to provide a white solid 6.90 g with a yield of 90.11%.

ESI-MS (m/z): 426 (M+H), 448 (M+Na);
¹HNMR (400 MHz, CDCl₃) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 9

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in dimethylbenzene (30 mL), and the solution of 3-fluoro-4-morpholinophenyl isocyanate in dimethylbenzene (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.28 g with a yield of 95.07%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 10

The Preparation of (S)-2-((3-(3-fluoro-4-morpholinophenyl)-2-oxo-5-oxazoline) methyl)isoindole-1,3-dione Anhydrous n-butylammonium bromide (0.4 g) and (S)-2-(oxiran-2-ylmethylene) isoindole-1,3-dione (3.66 g) were respectively dissolved in DMF (30 mL), and the solution of 3-fluoro-4-morpholinophenyl isocyanate in DMF (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.21 g with a yield of 94.15%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 11

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in isoamyl acetate (30 mL), and the solution of 3-fluoro-4-morpholinophenyl isocyanate in dimethylbenzene (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.39 g with a yield of 96.51%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 12

The Preparation of (S)-2-((3-(3-fluoro-4-morpholinophenyl)-2-oxo-5-oxazoline) methyl)isoindole-1,3-dione Anhydrous lithium bromide (0.9 g) and (S)-2-(oxiran-2-ylmethylene)isoindole-1,3-dione (3.66 g) were respectively dissolved in butyl acetate (30 mL), and the solution of 3-fluoro-4-morpholinophenyl isocyanate in dimethylbenzene (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.30 g with a yield of 95.33%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 13

The Preparation of (S)-2-((3-(3-fluoro-4-morpholinophenyl)-2-oxo-5-oxazoline) methyl)isoindole-1,3-dione Anhydrous magnesium bromide (1.0 g) and (S)-2-(oxiran-2-ylmethylene)isoindole-1,3-dione (3.66 g) were respectively dissolved in isoamyl acetate (30 mL), and the solution of 3-fluoro-4-morpholinophenyl isocyanate in DMF (4.0 g, 20 mL) was added. The reaction was performed at 120° C. for 4 h. To the reaction solution was added 60 mL of water and filtered. The filter cake was washed with cold petroleum ether (10 mL×2) and dried to provide a white solid 7.36 g with a yield of 96.11%.

ESI-MS (m/z): 426 (M+H), 448 (M+Na);
$^1$HNMR (400 MHz, CDCl$_3$) δ: 3.04 (m, 4H), 3.84 (m, 4H), 3.95 (m, 2H), 4.08 (m, 2H), 4.95 (m, 1H), 6.90 (t, 1H), 7.1 (m, 1H), 7.37 (dd, 1H), 7.75 (m, 2H), 7.87 (m, 2H).

Example 14

The Preparation of (S)-5-((dibenzylamino)methyl)-3-(3-fluoro-4-morpholino phenyl)-isooxazol-2-one (I-2)

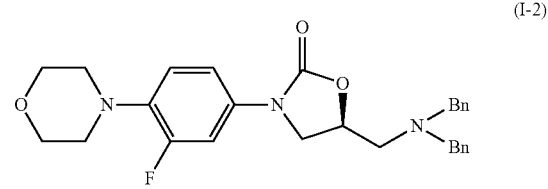 [SMILES: O=C1O[C@@H](CN(Cc2ccccc2)Cc2ccccc2)CN1c1ccc(N2CCOCC2)c(F)c1]

(I-2)

As the process described in Example 1, (S)-5-((dibenzylamino)methyl)-3-(3-fluoro-4-morpholinophenyl)-isooxazol-2-one was prepared by reacting 3-fluoro-4-morpholinophenyl isocyanate with (S)—N,N-dibenzylamino epoxy propylamine, with a yield of 75%.

ESI-MS (m/z): 476 (M+H);
$^1$HNMR (400 MHz, CDCl$_3$) δ: 2.86 (m, 2H), 3.10 (t, 4H), 3.42 (m, 1H), 3.59 (m, 4H), 3.68 (m, 1H), 3.86 (t, 4H), 4.55 (m, 1H), 6.88 (m, 1H), 7.01 (m, 1H), 7.22-7.34 (m, 11H).

Example 15

The Preparation of (S)-5-((N,N-di-tert-butoxycarbonylamino)methyl)-3-(3-fluoro-4-morpholinophenyl)-isooxazol-2-one (I-3)

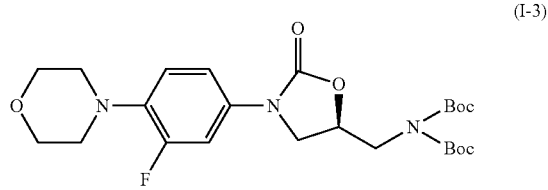 [SMILES: CC(C)(C)OC(=O)N(C[C@H]1CN(c2ccc(N3CCOCC3)c(F)c2)C(=O)O1)C(=O)OC(C)(C)C]

(I-3)

As the process described in Example 1, (S)-5-((N,N-di-tert-butoxycarbonylamino)methyl)-3-(3-fluoro-4-morpholinophenyl)-isooxazol-2-one was prepared by reacting 3-fluoro-4-morpholinophenyl isocyanate with (S)—N,N-di-tert-butoxycarbonyl epoxy propylamine, with a yield of 65%.

ESI-MS (m/z): 496 (M+H);

$^1$HNMR (400 MHz, CDCl$_3$) δ: 1.40 (s, 18H), 3.08-3.35 (m, 6H), 3.60-3.85 (m, 6H), 5.25 (m, 1H), 6.72 (d, 1H), 6.89 (d, 1H), 7.60 (d, 1H).

The invention claimed is:

1. A process for preparing an intermediate of Linezolid of Formula (I):

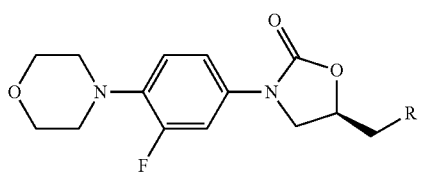

the process comprises the following steps:

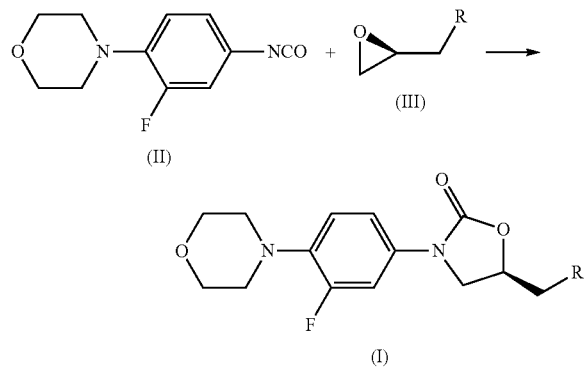

a cyclization reaction of 3-fluoro-4-morpholinophenyl isocyanate (II) and epoxy compound (III) is performed to obtain the compound of Formula (I), wherein R is a protected amino group as follows:

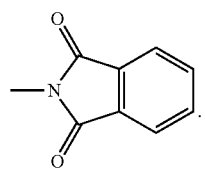

2. The process according to claim 1, wherein the cyclization reaction is performed in the presence of a catalyst, preferably, the catalyst is a Lewis acid or a mixture thereof.

3. The process according to claim 2, wherein the catalyst is selected from lithium bromide, magnesium bromide, lithium chloride, magnesium chloride, magnesium iodide, lithium iodide, lithium chloride, zinc chloride, tetra-n-butylammonium bromide, tetra-n-butylammonium chloride, or any mixture thereof.

4. The process according to claim 2, wherein the catalyst is selected from lithium bromide, magnesium bromide, magnesium iodide, or any mixture thereof.

5. The process according to claim 1, wherein the cyclization reaction is performed in a solvent, preferably, the solvent is an aprotic solvent or a mixture thereof.

6. The process according to claim 5, wherein the aprotic solvent includes but not limited to petroleum ether, ethyl acetate, isoamyl acetate, butyl acetate, toluene, xylene, chlorobenzene, tetrahydrofuran, dichloromethane, N, N-dimethylformamide, C$_6$-C$_8$ alkanes, acetone, 1,4-dioxane, acetonitrile, or any mixture thereof.

7. The process according to claim 1, wherein the temperature of the cyclization reaction is in the range of 60° C.-150° C.

8. The process according to claim 7, wherein the temperature of the cyclization reaction is in the range of 100-140° C., particularly preferably 115-125° C.

9. A process for preparing linezolid, wherein linezolid is prepared from the intermediate of Formula (I)

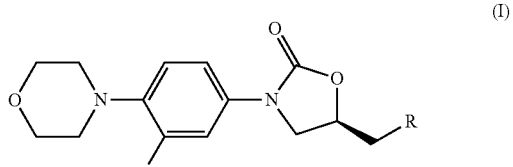

wherein the intermediate of Formula (I) is prepared by the reaction as follows:

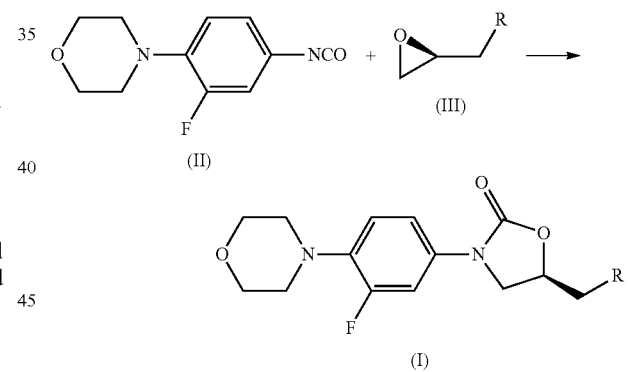

a cyclization reaction of 3-fluoro-4-morpholinophenyl isocyanate (II) and epoxy compound (III) is performed to obtain the compound of Formula (I), wherein R is a protected amino group as follows:

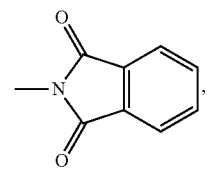

followed by deprotection and acetylation to obtain linezolid.

* * * * *